US012133624B2

(12) United States Patent
Park et al.

(10) Patent No.: US 12,133,624 B2
(45) Date of Patent: Nov. 5, 2024

(54) ROBOT CLEANER AND METHOD FOR CONTROLLING SAME

(71) Applicant: Samsung Electronics Co., Ltd., Suwon-si (KR)

(72) Inventors: Jangpyo Park, Suwon-si (KR); Seonghwan Kim, Suwon-si (KR); Yongwon Jeong, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 833 days.

(21) Appl. No.: 17/286,773

(22) PCT Filed: Oct. 23, 2019

(86) PCT No.: PCT/KR2019/013954
§ 371 (c)(1),
(2) Date: Apr. 19, 2021

(87) PCT Pub. No.: WO2020/096232
PCT Pub. Date: May 14, 2020

(65) Prior Publication Data
US 2021/0338028 A1    Nov. 4, 2021

(30) Foreign Application Priority Data

Nov. 8, 2018  (KR) ........................ 10-2018-0136778

(51) Int. Cl.
*B25J 9/00*      (2006.01)
*A47L 9/28*      (2006.01)
*G01N 33/00*   (2006.01)

(52) U.S. Cl.
CPC ............. *A47L 9/281* (2013.01); *A47L 9/2852* (2013.01); *A47L 9/2894* (2013.01);
(Continued)

(58) Field of Classification Search
CPC ...... A47L 9/281; A47L 9/2852; A47L 9/2894; A47L 2201/04; A47L 9/2826;
(Continued)

(56) References Cited

U.S. PATENT DOCUMENTS 6,732,826 B2   5/2004  Song et al.
9,399,284 B2   7/2016  Kwon et al.
(Continued)

FOREIGN PATENT DOCUMENTS

EP       3345525 A1     7/2018
JP   2007-029489 A     2/2007
(Continued)

OTHER PUBLICATIONS

International Search Report dated Feb. 20, 2020 in connection with International Patent Application No. PCT/KR2019/013954, 2 pages.
(Continued)

*Primary Examiner* — Ian Jen

(57) ABSTRACT

Disclosed is a robot cleaner. The robot cleaner of the present disclosure comprise: a gas sensor which is disposed inside the robot cleaner and senses suctioned air; and a processor which identifies contaminants on the basis of a sensing value of the gas sensor, and controls the robot cleaner so that the robot cleaner travels while avoiding the identified contaminants.

15 Claims, 11 Drawing Sheets

(52) U.S. Cl.
CPC ...... *G01N 33/0031* (2013.01); *A47L 2201/04* (2013.01); *G05B 2219/45098* (2013.01)

(58) Field of Classification Search
CPC . A47L 9/2847; A47L 9/2805; G01N 33/0031; G01N 33/00; G01N 33/0027; G05B 2219/45098; B25J 9/16; B25J 11/00; B25J 9/1664; B25J 11/0085; G05D 1/02; G05D 1/0214
See application file for complete search history.

(56) References Cited

U.S. PATENT DOCUMENTS

| | | | |
|---|---|---|---|
| 10,368,708 B2 * | 8/2019 | Cornelissen | .......... A47L 9/2826 |
| 10,427,085 B2 | 10/2019 | Kim et al. | |
| 10,849,471 B2 | 12/2020 | So et al. | |
| 2012/0259481 A1 | 10/2012 | Kim | |
| 2014/0230179 A1 * | 8/2014 | Matsubara et al. | ....... A47L 7/04 15/319 |
| 2015/0134179 A1 * | 5/2015 | Murakami et al. | ..... A47L 9/009 |
| 2017/0090456 A1 | 3/2017 | Mao et al. | |
| 2018/0125318 A1 | 5/2018 | Cornelissen | |

FOREIGN PATENT DOCUMENTS

| | | |
|---|---|---|
| JP | 2013-081604 A | 5/2013 |
| JP | 2018515191 A | 6/2018 |
| KR | 10-0406636 B1 | 11/2003 |
| KR | 10-0700920 B1 | 3/2007 |
| KR | 10-0781089 B1 | 11/2007 |
| KR | 10-0963783 B1 | 6/2010 |
| KR | 10-2014-0096692 A | 8/2014 |
| KR | 10-2016-0043279 A | 4/2016 |
| KR | 10-2018-0046499 A | 5/2018 |

OTHER PUBLICATIONS

Written Opinion of the International Searching Authority dated Feb. 20, 2020 in connection with International Patent Application No. PCT/KR2019/013954, 4 pages.

Notice of Final Rejection issued Sep. 8, 2023, in connection with Korean Patent Application No. 10-2018-0136778, 8 pages.

Request for the Submission of an Opinion issued Mar. 24, 2023, in connection with Korean Patent Application No. 10-2018-0136778, 10 pages.

* cited by examiner

CENTER OF
INSCRIBED CIRCLE
(3.067 , 6.252)

(a)

CENTER OF
CIRCUMSCRIBED CIRCLE
(4.955 , 5.773)

(b)

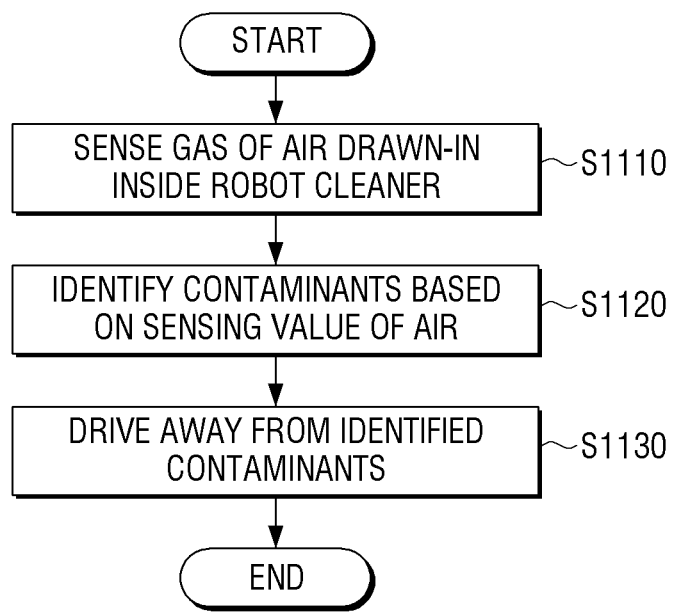

ROBOT CLEANER AND METHOD FOR CONTROLLING SAME

CROSS-REFERENCE TO RELATED APPLICATIONS

This application is a 371 of International Application No. PCT/KR2019/013954 filed on Oct. 23, 2019, which claims priority to Korean Patent Application No. 10-2018-0136778 filed on Nov. 8, 2018, the disclosures of which are herein incorporated by reference in their entirety.

BACKGROUND

1. Field

The disclosure relates to a robot cleaner and a method for controlling the same. More particularly, the disclosure relates to a robot cleaner configured to identify contaminants by using a gas sensor, and drive avoiding identified contaminants and a method for controlling the same.

2. Description of Related Art

Development of robots have made for provision of robots ubiquitous in not only specialized academic fields or industrial fields requiring a workforce of a mass scale, but also in typical households.

In particular, because a robot cleaner (or, a cleaning robot), as a device which automatically cleans a cleaning area by drawing-in foreign substances such as dust of a surface to be cleaned while driving on its own on an area to be cleaned, relieves time and effort spent in household chores of a user, it is most sought-after in the market and familiar to minds of people.

However, in the case of robot cleaners of related art which identifies obstacles by a camera or a contact sensor, there is the disadvantage of not being able to detect liquid types or contaminants that are not hard and passing through the contaminants generating a greater stain. In addition, when the robot cleaner passes through the contaminants, there is the disadvantage of contaminants being drawn into the robot cleaner and being the cause of malfunctions of the robot cleaner.

Aspects of the disclosure are to address at least the above-mentioned problems and/or disadvantages and to provide at least the advantages described below. Accordingly, an aspect of the disclosure is to provide a robot cleaner which drives avoiding (away from) identified contaminants by using a gas sensor and transmits information on the contaminants to the user for a prompt removal of the contaminants and a method for controlling the same.

SUMMARY

According to an embodiment of the disclosure, a robot cleaner includes a gas sensor disposed inside of the robot cleaner and configured to sense drawn-in air and a processor configured to identify contaminants based on a sensing value of the gas sensor, and control the robot cleaner to drive avoiding the identified contaminants.

In this case, a main flow path through which air drawn-in from the outside flows and a sub flow path which is branched from the main flow path, and through which a portion of air of the main flow path flows may be further included, and the gas sensor may be arranged at an end of the sub flow path, and configured to sense air flowing through the sub flow path.

In this case, a pump arranged in the sub flow path may be further included.

Meanwhile, the processor may be configured to reduce, based on a sensing value of the gas sensor being greater than or equal to a pre-set value, a driving speed of the robot cleaner.

In this case, the processor may be configured to control, based on a sensing value of the gas sensor being greater than or equal to a pre-set value, the robot cleaner to rotate left and right by a pre-set angle to obtain a sensing value from the gas sensor, and drive in a direction in which the obtained sensing value is less than the pre-set value.

In this case, the processor may be configured to identify, based on a sensing value of the gas sensor being greater than or equal to a pre-set value, a position of the contaminants and a size of an area based on a driving route.

In this case, a communicator configured to communicate with an external device nay be further included, and the processor may be configured to transmit information on the identified position of the contaminants and the size of the area to the external device.

Meanwhile, a second gas sensor arranged at an outer front surface of the robot cleaner based on a driving direction of the robot cleaner may be further included.

In this case, the second gas sensor may be arranged at a left side and a right side of the front surface of the robot cleaner, and the processor may be configured to control, based on a sensing value of the second gas sensor of at least one of the left side or the right side being greater than or equal to a pre-set value, the robot cleaner to drive in a direction in which the sensing value is less than the pre-set value.

Meanwhile, the processor may be configured to analyze a type of gas based on a value sensed by the gas sensor, and identify a type of contaminants based on the type of gas.

Meanwhile, according to an embodiment of the disclosure, a method for controlling a robot cleaner includes sensing gas in air drawn-in inside of the robot cleaner by using a gas sensor disposed inside of the robot cleaner, identifying contaminants based on a sensing value of the air, and driving avoiding (away from) the identified contaminants.

In this case, the gas sensor may be arranged at an end of a sub flow path which is branched from a main flow path through which the drawn-in air flows and through which a portion of air of the main flow path flows, and the sensing may include sensing air flowing in the sub flow path.

In this case, the sensing may further include introducing air flowing in the sub flow path to the gas sensor by using a pump arranged at the sub flow path.

Meanwhile, the driving may include reducing, based on a sensing value of the gas sensor being greater than or equal to a pre-set value, a driving speed of the robot cleaner.

In this case, the driving may include rotating, based on a sensing value of the gas sensor being greater than or equal to a pre-set value, left and right by a pre-set angle to obtain a sensing value from the gas sensor, and driving in a direction in which the obtained sensing value is less than the pre-set value.

In this case, identifying, based on a sensing value of the gas sensor being greater than or equal to a pre-set value, a position of the contaminants and a size of an area based on a driving route may be further included.

In this case, transmitting information on the identified position of the contaminants and the size of the area to an external device may be further included.

Meanwhile, sensing, based on a driving direction of the robot cleaner, gas in air outside of the robot cleaner by using a second gas sensor arranged at an outer front surface of the robot cleaner may be further included.

In this case, the second gas sensor may be arranged at a left side and a right side of the front surface of the robot cleaner, and the method may further include driving, based on a sensing value of the second gas sensor of at least one of the left side or the right side being greater than or equal to a pre-set value, in a direction in which the sensing value is less than the pre-set value.

Meanwhile, analyzing a type of gas based on a value sensed by the gas sensor and identifying a type of contaminants based on the type of gas may be further included.

BRIEF DESCRIPTION OF THE DRAWINGS

FIG. 11 is a flowchart illustrating a control method of a robot cleaner according to an embodiment of the disclosure.

DETAILED DESCRIPTION

Figure 1:
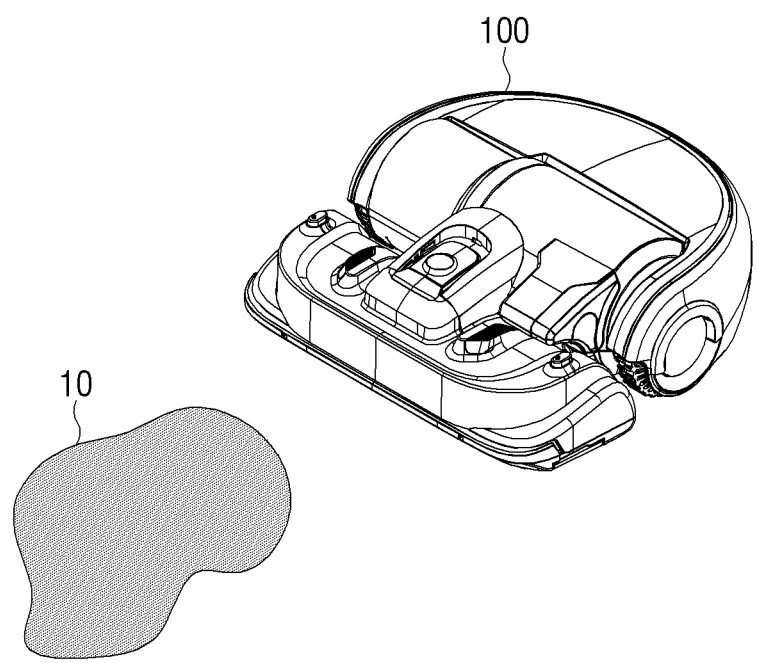
FIG. 1 is a diagram illustrating an embodiment of using a robot cleaner according to the disclosure.

The terms used in the disclosure will be briefly described, and the disclosure will be described in detail.

The terms used in the embodiments of the disclosure are general terms identified in consideration of the functions in the disclosure. However, these terms may vary depending on intention, legal or technical interpretation, emergence of new technologies, and the like of those skilled in the related art. Also, there may be some terms arbitrarily identified by an applicant, and in this case the meaning thereof will be described in detail in the description part of the corresponding disclosure. Accordingly, the terms used herein may be construed, not simply by their designations, but based on the meaning of the term and the overall content of the disclosure.

Various modifications may be made to the embodiments of the disclosure, and there may be various types of embodiments. Accordingly, specific embodiments will be illustrated in drawings, and described in detail in the detailed description. However, it should be noted that the various embodiments are not for limiting the scope of the disclosure to a specific embodiment, but they should be interpreted to include all modifications, equivalents or alternatives of the embodiments included in the ideas and the technical scopes disclosed herein. Meanwhile, in case it is determined that in describing embodiments, detailed description of related known technologies may unnecessarily confuse the gist of the disclosure, the detailed description will be omitted.

Terms such as "first," and "second" may be used in describing the various elements, but the elements are not to be limited by the terms. The terms may be used only to distinguish one element from another.

A singular expression includes a plural expression, unless otherwise specified. It is to be understood that the terms such as "comprise" or "include" are used herein to designate a presence of a characteristic, number, step, operation, element, component, or a combination thereof, and not to preclude a presence or a possibility of adding one or more of other characteristics, numbers, steps, operations, elements, components or a combination thereof.

In the embodiments of the disclosure, a "module," a "unit," or a "part" may perform at least one function or operation, and may be implemented as a hardware or a software, or a combination of the hardware and the software. Further, except for when each of a plurality of "modules," "units," or "parts" need to be implemented in an individual hardware, the components may be integrated in at least one module and implemented in at least one processor.

Example embodiments of the disclosure will be described in detail with reference to the accompanying drawings to aid in the understanding of those of ordinary skill in the art. However, the disclosure may be realized in various different forms and it should be noted that the disclosure is not limited to the various example embodiments described herein. Further, in the drawings, parts not relevant to the description may be omitted, and like reference numerals may be used to indicate like elements.

The disclosure will be described in greater detail below with reference to the accompanied drawings.

FIG. 1 is a diagram illustrating an embodiment of using a robot cleaner according to the disclosure.

Referring to FIG. 1, the robot cleaner 100 may clean the surface to be cleaned of a space in which itself is to be installed. For example, the robot cleaner 100 may be installed at an inner space of a house, and the robot cleaner 100 may draw-in air while moving according to a pre-set pattern or a command set/input by the user, and collect dust surrounding the surface to be cleaned.

In particular, the robot cleaner 100 according to the disclosure may sense the contaminants 10 present within the space and drive avoiding the same. Specifically, the robot cleaner 100 may sense the contaminants 10 by using the provided gas sensor.

Here, the contaminants 10 may be excrements of a pet, a liquid type such as water or juice, a food product, or the like. The contaminants 10 may not have been sensed by robot cleaners of the related art which avoids obstacles by using a contact sensor.

In addition, the robot cleaner 100 of the disclosure may not only avoid the contaminants 10, but also identify a position and an area size of the contaminants 10, and transmit the identified result to an external device such as a user terminal device.

The specific operation of the robot cleaner 100 will be described in detail below with reference to FIGS. 2 to 12.

Figure 2:
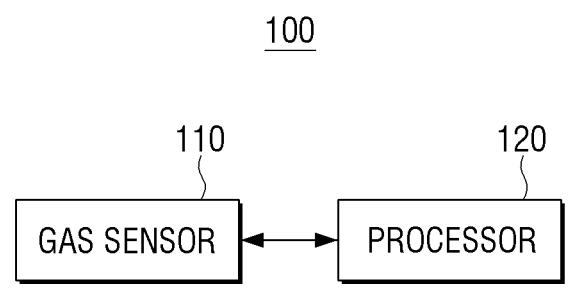
FIG. 2 is a block diagram illustrating a schematic configuration of a robot cleaner according to an embodiment of the disclosure.

FIG. 2 is a block diagram illustrating a schematic configuration of a robot cleaner according to an embodiment of the disclosure.

Referring to FIG. 2, the robot cleaner 100 may include a gas sensor 110 and a processor 120.

The gas sensor 110 may, as a configuration for measuring a concentration of a specific gas, be included outside or inside of the robot cleaner 100 and used in measuring contaminants such as volatile organic compounds (VOC).

Here, the gas sensor 110 may be a semiconductor gas sensor, but any sensor capable of detecting a concentration of gas in the air may be included in the disclosure.

The gas sensor 110 may include a gas sensing material which changes electrical or physical properties based on being exposed to gas.

As the gas sensing material, a semiconductor material such as, for example, and without limitation, $SnO_2$, ZnO, $WO_3$, $TiO_2$, $In_2O_3$, Pd, $Fe_2O_3$, $ThO_2$, AlN, $ZrO_2$, CoO, $LaAlO_3$, $Co_3O_4$, NiO, CuO, or the like may be used, but is not limited thereto. A precious metal catalyst may be further included to the gas sensing material. The catalyst may not only improve sensitivity and reaction rate but also raise selectivity with respect to a specific gas. In addition to the above, an oxide may be added to adjust resistance or enhance selectivity, stability, or the like.

The gas sensor 110 may be formed in a bulk type, or may be formed in a thick film form on a substrate through a screen printing method, or formed in a thin film form on a substrate through a chemical vapor deposition method, a sputtering method, a sol-gel method, or the like. The electronic device 100 may include an electrode which outputs changes in electric conductivity in the gas sensor 110 as electric signals. As materials of the electrode, tungsten, silver, platinum, gold, and the like may be used as an example. The type of electrode may be divided into a measuring electrode, a heater combined use electrode, or the like, and forms of the electrode may include, for example, a transparent electrode.

Meanwhile, the gas sensor 110 may be in plurality, and gas sensors of different types with one another may be used. Accordingly, the type and concentration of gas may be obtained by analyzing sensing values of gas sensors different from one another.

Specifically, the gas sensor 110 may be attached to the outside of the robot cleaner 100 and sense the gas of the outside air. At this time, the gas sensor 110 may be arranged at an outer front surface of the robot cleaner 100 based on a driving direction of the robot cleaner 100. Here, the front surface may refer to the outermost front surface in terms of the driving of the robot cleaner 100.

For example, the gas sensor 110 may be arranged at a center front surface of the robot cleaner 100. In another embodiment, the gas sensors 110 may each be arranged at a left side front surface and a right side front surface of the robot cleaner 100. In still another embodiment, the gas sensors 110 may each be arranged at the center front surface and at both sides of the robot cleaner 110. Information on the directionality of the contaminants sensed by the arrangement of the gas sensors 110 may be quickly obtained.

Meanwhile, in case the gas sensor 110 is arranged at a side surface and not the front surface of the robot cleaner 100 based on the driving direction of the robot cleaner 100, there is the possible that the contaminants present on a driving route of the robot cleaner 100 may not be sensed.

As described above, based on arranging the gas sensor 110 at the outer front surface of the robot cleaner 100, a sensing sensitivity of contaminants may be improved.

Meanwhile, the gas sensor 110 may be arranged (disposed) inside of the robot cleaner 100 and may sense the air drawn-in from the outside. Here, the gas sensor 110 may be arranged at various positions inside the robot cleaner 100. For example, the gas sensor 110 may be arranged on a suction port through which air is drawn-in (inhaled), or arranged on a main flow path through which the drawn-in air flows.

As described above, in case the gas sensor 110 senses the gas of the drawn-in air, the presence of contaminants may be detected in advance because air of a further distance may be sensed based on air being drawn-in. In addition, based on the gas sensor 110 being arranged in a closed space inside of the robot cleaner 100, efficiency in gas sensing may be improved.

Meanwhile, if necessary, the robot cleaner 100 may further include a sub flow path which is branched from the main flow path, and through which a portion of the air of the main flow path flows. The gas sensor 110 may be arranged at an end of the sub flow path, and may sense the air introduced through the sub flow path.

At this time, the air introduced through the sub flow path may be such that only a certain flow amount of the air flowing through the main flow path flows at a low flow rate. Based on arranging the gas sensor 110 at the end of the sub flow path as described above, a low sensing accuracy of when the flow rate of air flowing through the main flow path is too fast may be overcome.

Meanwhile, if necessary, the robot cleaner 100 may further include a pump which is arranged on the sub flow path. Here, the pump may be a configuration for introducing air to the gas sensor 110 in case sensing is difficult as a result of a flow amount and a flow rate of air flowing through the sub flow path being too low. The pump may further draw-in air from the main flow path and provide air with improved flow amount and flow rate to the gas sensor 110.

Meanwhile, in the above, the gas sensor 110 has been described as being arranged outside or inside of the robot cleaner, but may be arranged at the outside and the inside. The various arrangements of the gas sensor 110 will be described in detail with reference to FIGS. 4 and 8.

The processor 120 may control the overall operation of the robot cleaner 100.

The processor 120 according to an embodiment may be implemented as a digital signal processor (DSP), a microprocessor, or a time controller (TCON). However, the embodiment is not limited thereto, and may include, for example, and without limitation, one or more from among a central processing unit (CPU), a micro controller unit (MCU), a micro processing unit (MPU), a controller, an application processor (AP), a communication processor (CP), an ARM processor, or the like, or may be defined by the corresponding term. In addition, the processor 120 may be implemented as a System on Chip (SoC) or large scale integration (LSI) embedded with a processing algorithm, and may be implemented in the form of a field programmable gate array (FPGA).

Specifically, the processor 120 may detect the presence of contaminants based on a sensing value of the gas sensor 110. At this time, the processor 120 may analyze the type and concentration of the gas based on the sensing value. Then, the processor 120 may identify the presence of contaminants and the type of the contaminants according to an analyzed result. For example, if the concentration of ammonia is greater than or equal to a pre-set value based on the sensing value obtained by the gas sensor 110, the processor 120 may identify the contaminants as urine. Alternatively, if the concentration of sulfur compounds is greater than or equal to a pre-set value based on the sensing value obtained by the gas sensor 110, the processor 120 may identify the contaminants as excrement. Specifically, the processor 120 may comprehensively analyze the value sensed by the gas sensors 110 arranged inside and outside of the robot cleaner 100 and identify the presence of the contaminants and the type of the contaminants.

Then, the processor 120 may be configured to control, based on contaminants being present, the robot cleaner 100 to drive avoiding the contaminants. The driving operation of the robot cleaner 100 will be described in detail below with reference to FIGS. 3 and 9.

Figure 3:
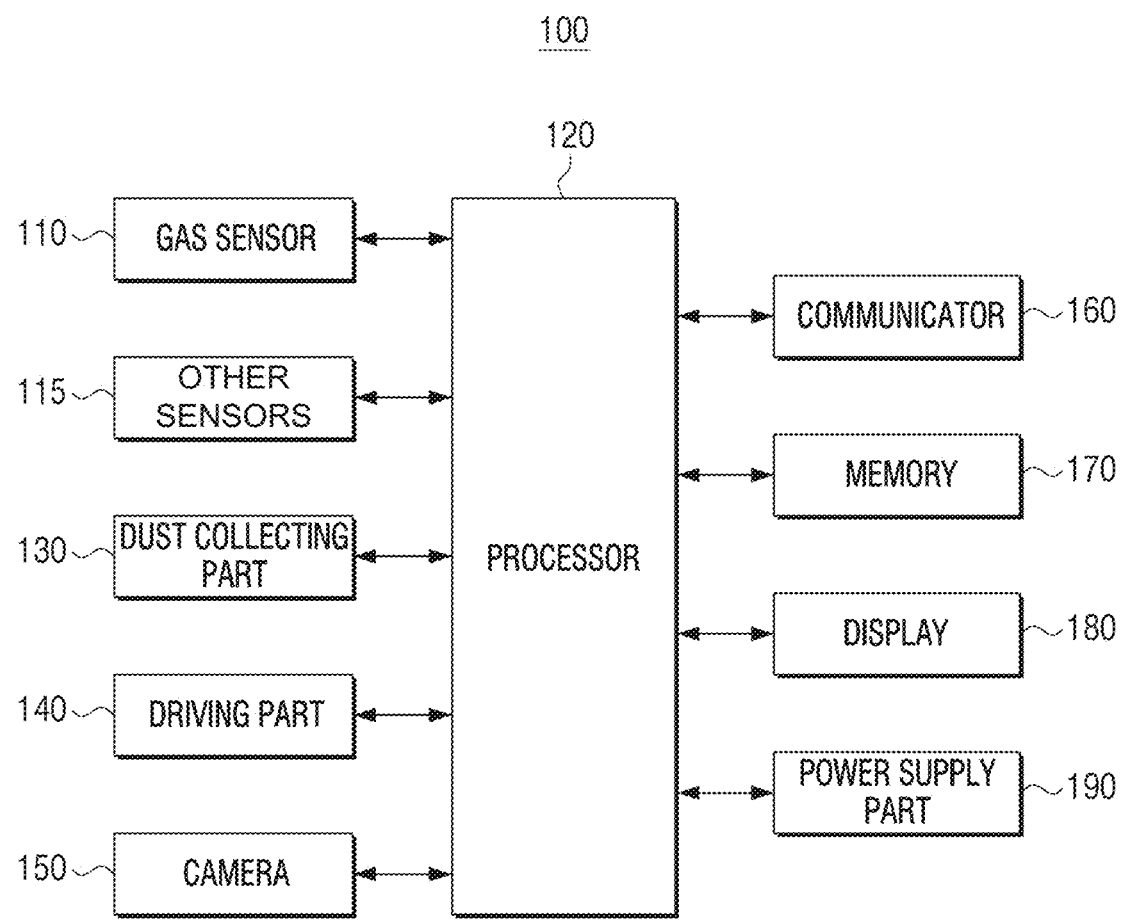
FIG. 3 is a block diagram illustrating a detailed configuration of the robot cleaner as shown in FIG. 2.

FIG. 3 is a block diagram illustrating a detailed configuration of the robot cleaner as shown in FIG. 2.

Referring to FIG. 3, the robot cleaner 100 may include a gas sensor 110, other sensors 115, a processor 120, a dust collecting part 130, a driving part 140, a camera 150, a communicator 160, a memory 170, a display 180 and a power supply part 190.

Here, because the gas sensor 110 is the same as the configuration illustrated in FIG. 2, redundant descriptions will be omitted.

The other sensors 115 may include various sensors other than the gas sensor 110. Specifically, the other sensors 115 may detect an external environment and its state to perform a cleaning function and an information providing function of the robot cleaner 100.

For example, the other sensors 115 may include a temperature sensor, and humidity sensor. At this time, the processor 120 may, in addition to the sensing value of the gas sensor 110, further consider the sensing value of a temperature sensor or a humidity sensor in addition to the sensing value of the gas sensor 110, and identify whether there is liquid in the contaminants and the type of the contaminants. For example, based on ammonia being detected by the gas sensor 110 and a humidity sensing value by the humidity sensor being high, the processor 120 may identify the contaminants as urine. Meanwhile, based on sulfur compounds being detected by the gas sensor 110 and the humidity sensing value by the humidity sensor being high, the processor 120 may identify the contaminants as excrement. Meanwhile, based on the sensing value by the gas sensor 110 being low and the humidity sensing value by the humidity sensor being high, the processor 120 may identify the contaminants as water.

The other sensors 115 may include at least one obstacle sensor for detecting obstacles. The obstacle sensor may include a non-contact type detection sensor and a contact-type collision/bumper sensor capable of identifying walls, gaps, pillars, doorsills, mounds, or the like which the robot cleaner 100 is unable to pass through.

The other sensors 115 may include a dust sensor which detects the concentration of dust drawn-in through the suction port of the robot cleaner 100.

The other sensors 115 may include a human detection sensor capable of recognizing persons. For example, the other sensors 115 may detect infrared changes of a surrounding environment and generate a signal capable of determining whether a person is in movement in front thereof.

The other sensors 115 may include a sensor detecting an inner state. Examples include a current sensor which detects a degree of dust collected in the dust container or a load to the motor increasing because of foreign substances caught on a wheel, a sensor detecting an over-charge of a battery, a sensor detecting a foreign substance on the sensor window through which signals of sensors detecting the external environment are emitted, or the like.

The other sensors 115 are not limited by the above-described examples, and may be variously added/changed according to necessity and design.

The dust collecting part 130 may collect dust. Specifically, the dust collecting part 130 may draw-in air, and collect the dust of the drawn-in air. The dust collecting part 130 may include a motor which passes air through a guide pipe that extends from the suctioning part to an air discharge port, a filter which filters dust of the drawn-in air, a dust container which contains the filtered dust, and the like.

The driving part 140 may drive or rotate the robot cleaner 100. Specifically, the driving part 140 may move the robot cleaner 100 to an area to be cleaned by the control of the processor 120. The driving part 140 may include at least one wheel which contacts with a floor surface, a motor for providing power to the wheel, a driver for controlling the motor, and the like.

Specifically, the processor 120 may be configured to reduce a driving speed of the robot cleaner 110 if the value sensed by the gas sensor 110 is greater than or equal to a pre-set value. As described above, by reducing a moving speed of the robot cleaner 100, the gas sensor 110 may secure the time for detecting the gas discharged from the contaminants.

For example, based on the gas sensor 110 being arranged at the center or inside of the outer front surface of the robot cleaner 100, if the sensing value of the gas sensor 110 is greater than or equal to a pre-set value, the processor 120 may be configured to control the driving part 140 for the robot cleaner to rotate left and right by a pre-set angle. Then, the processor 120 may be configured to control the driving part 140 to drive in a direction with a low sensing value from among the sensing value when rotated to a left direction and a sensing value when rotated to a right direction. This is because the direction with the low sensing value has a low likelihood of contaminants being present.

Specifically, the processor 120 may be configured to control the driving part 140 to drive in a direction in which the sensing value is less than a pre-set value.

Meanwhile, the processor 120 may be configured to control, after moving in a direction with a low sensing value, the driving part 140 for the robot cleaner 100 to rotate left and right by a pre-set angle, and repeat the driving operation in a direction with the low sensing value. At this time, the processor 120 may be configured to track, based on controlling the robot cleaner 100 to roam the surrounding of the contaminants, the position and size of the contaminants. Specifically, the driving route may be obtained by tracking a direction in which the sensing value is less than a pre-set value. As described above, the processor 120 may be configured to identify, based on the driving route of the robot cleaner 100, the position of the contaminants and the size of the area of the contaminants.

Meanwhile, based on the gas sensor 110 being arranged at both sides of the outer front surface of the robot cleaner 100, if one sensing value from among the gas sensor arranged at the left side and the gas sensor arranged at the right side is greater than or equal to a pre-set value, the processor 120 may be configured to control the driving part 140 to drive in a direction with the low sensing value.

Even in this case, the processor 120 may be configured to repeat, after moving in a direction with the low sensing value, the operation of driving in a direction with the low sensing value again. The processor 120 may be configured to track the position and size of the contaminants by controlling the robot cleaner 100 to roam the surrounding of the contaminants. As described above, the processor 120 may identify, based on the driving route of the robot cleaner, the position of the contaminants and the size of the area of the contaminants.

The camera 150 may photograph an image. Specifically, the camera 150 may photograph an image outside the robot cleaner 100. The camera 150 may include a ceiling camera.

The ceiling camera may generate an image data which is to be a reference so that the position to which the robot cleaner 100 moves may be tracked.

The camera 150 may include a front camera. The front camera may photograph a subject in front of the robot cleaner 100. The photographed image of the front may be used for the purposes of avoiding obstacles on the route the robot cleaner 100 moves, calculating an optimized moving route, or surveilling the indoors. Specifically, the processor 120 may be configured to identify the presence and type of the contaminants at the front by using the sensing value of the gas sensor 110 and the image of the camera 150. At this time, the operation of identifying the type of contaminants by using the image may be performed by using an artificial intelligence model of an external server.

The communicator 160 may be a configuration for performing communication with external devices of various types according to communication methods of various types. Here, the external device communicating with the robot cleaner 100 may be a server, a user terminal device, or the like. The processor 120 may be configured to transmit information on the position of the identified contaminants and the size of the area to the external device through the communicator 160.

The communicator 160 being communicatively connected with an external device may include communicating through a third device (e.g., a relay, a hub, an access point, a server, a gateway, etc.). The wireless communication may include a cellular communication which uses at least one from among, for example, and without limitation, a long term evolution (LTE), an LTE advance (LTE-A), a code division multiple access (CDMA), a wideband CDMA (WCDMA), a universal mobile telecommunications system (UMTS), a wireless broadband (WiBro), a global system for mobile communications (GSM), or the like. According to an embodiment, the wireless communication may include at least one from among, for example, and without limitation, a wireless fidelity (WiFi), a Bluetooth, a Bluetooth low energy (BLE), a ZigBee, a near field communication (NFC), a magnetic secure transmission, a radio frequency (RF), a body area network (BAN), or a global positioning system (GPS). The wired communication may be a universal serial bus (USB), or the like. A network in which the wireless communication or the wired communication is performed may include a telecommunication network, for example, at least one from among a computer network (e.g., local area network (LAN) or wide area network (WAN)), the Internet, or a telephone network.

The memory 170 may store various programs and data necessary in the operation of the electronic device 100. Specifically, the memory 170 may be stored with at least one instruction. The processor 120 may perform the above-described operation by executing the stored instructions. The memory 170 may be implemented as a non-volatile memory, a volatile memory, a flash-memory, or the like.

The memory 170 may be stored with the gas sensing value and matching information on the gas type. In another embodiment, the gas sensing value and the matching information on the gas type may be received from an external server. At this time, the gas sensor 110 may be in plurality, and may include gas sensors of different types. The gas sensing value and the matching information on the gas type may be the result of pre-learning the sensing values of various gas sensors according to the gas types.

The memory 170 may be stored with information on a space to which the robot cleaner 100 moves. Examples may include a structure of a house, an arrangement structure of furniture, and the like. Information on the space may be obtained by a user input, by receipt from an external server, or learned from information obtained while the robot cleaner 100 is in movement.

The display 180 may display an image. At this time, the display 180 may be provided in the robot cleaner 100 and display a user interface (UI) screen implemented by the control of the processor 120. At this time, the display 180 may be a touch screen. In this case, a user command may be input through the display 180. According to the various embodiments, the display 180 may not be provided in the robot cleaner 100.

The power supply part 190 may supply power necessary in the driving of the robot cleaner 100. The power supply part 190 may be implemented as a secondary cell (or, referred to as a battery) capable of charging and discharging.

In addition thereto, although not illustrated in FIG. 3, the robot cleaner 100 may further include a speaker, an external input port for connecting with various external terminals, a button for receiving input of user operation, a microphone, or the like.

FIGS. 4 to 8 are diagrams illustrating various arrangements of a gas sensor.

Figure 4:
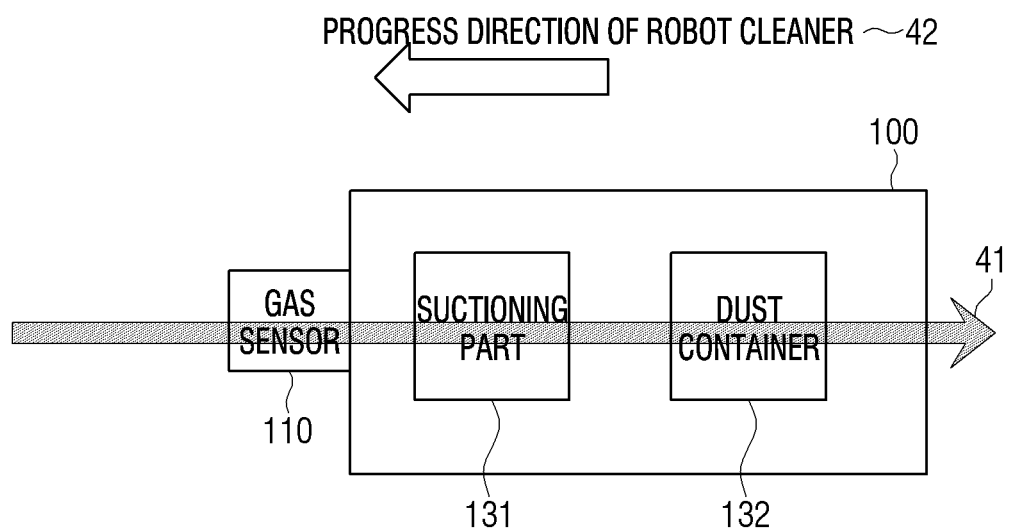
FIGS. 4 to 8 are diagrams illustrating various arrangements of a gas sensor.

Referring to FIG. 4, the gas sensor 110 may be arranged at an outer front surface of the robot cleaner 100. Specifically, the gas sensor 110 may be arranged at the outermost front surface based on a progress direction 42 of the robot cleaner.

Based on the suctioning part being operated, the progress direction of air 41 may be a direction diagonally opposite with the progress direction 42 of the robot cleaner. At this time, the outside air of the robot cleaner 100 may, after passing the gas sensor 110, be drawn-in to the inside of the robot cleaner 100 through the suctioning part 131 and discharged to the discharge port passing the dust container 132.

In FIG. 4, the gas sensor 110 has been illustrated as being arranged at a center of the outer front surface of the robot cleaner 100, but is not limited thereto, and the plurality of gas sensors ① and ② may be arranged at both sides of the outer front surface of the robot cleaner 100. Based on the plurality of gas sensors ① and ② being arranged at both sides, if the sensing value is greater than or equal to a pre-set value, the robot cleaner 100 may identify a direction in which the sensing value is low without having to perform the rotation.

Figure 5:
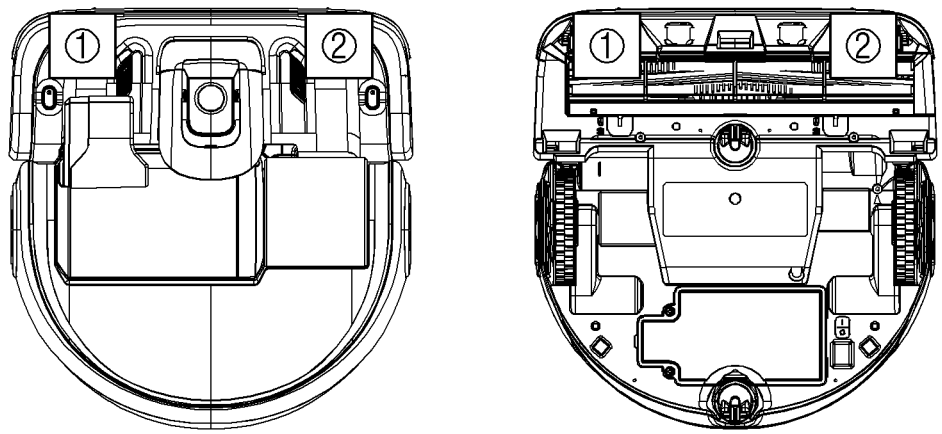

At this time, the plurality of gas sensors ① and ② according to an embodiment may be arranged, as illustrated in FIG. 5, at a front of a lower surface or a front of a upper surface of the robot cleaner 100 based on a driving direction of the robot cleaner 100. Based on the plurality of gas sensors ① and ② being arranged at the lower surface of the robot cleaner 100, the plurality of gas sensors ① and ② may be arranged at a surrounding of the suctioning part. Accordingly, based on the plurality of gas sensors ① and ② being arranged at the front of the upper surface or the front of the lower surface of the robot cleaner, the efficiency in gas sensing may be maintained while a risk of damage is reduced.

Figure 6:
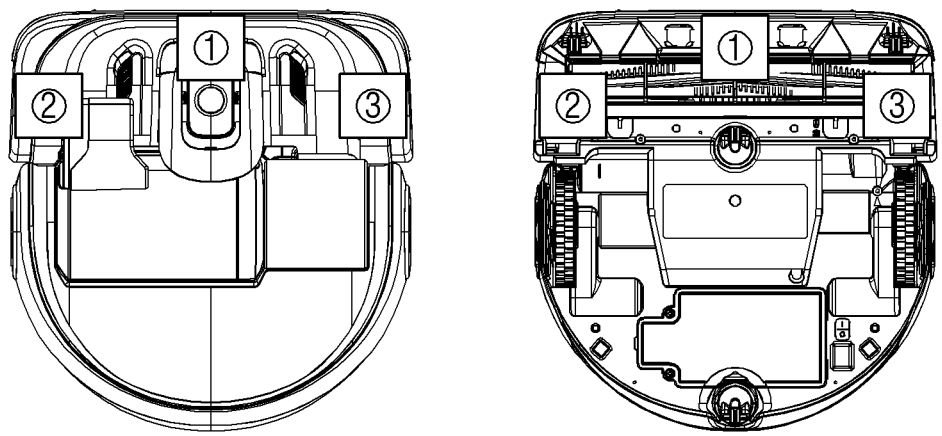

Meanwhile, as illustrated in FIG. 6 according to an embodiment, the plurality of gas sensors ①, ② and ③ may be arranged at a center and at both sides of the outer front surface of the robot cleaner 100.

Figure 7:
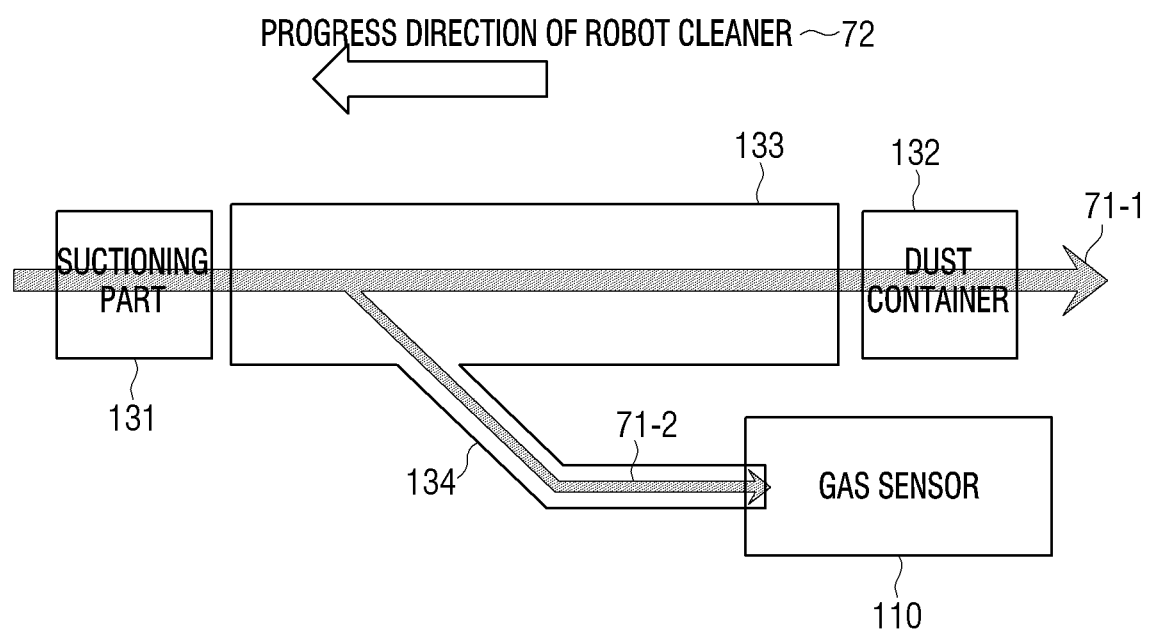

Referring to FIG. 7, the gas sensor 110 may be arranged at an end of a sub flow path 134 which is branched from a main flow path 133 through which the air suctioned from the outside through the suctioning part 131 flows. The air suctioned from the outside through the suctioning part 131 the air 71-1 which passes the main flow path 133 may be discharged through the discharge port passing the dust container 132. At this time, the progress direction of the air 71-1 which passes the main flow path 133 may be a direction diagonally opposite to the progress direction 42 of the robot cleaner.

At this time, a portion of the air 71-1 passing the main flow path 133 may flow to the sub flow path 71-2 and may be introduced to the gas sensor 110. At this time, the air which flows to the sub flow path 71-2 may have a low flow amount and flow rate than the air 71-1 flowing in the main flow path 133. Based on arranging the gas sensor 110 at the end of the sub flow path 134 as described above, the low sensing accuracy of when the flow rate of air flowing through the main flow path 133 is too fast may be overcome.

Figure 8:
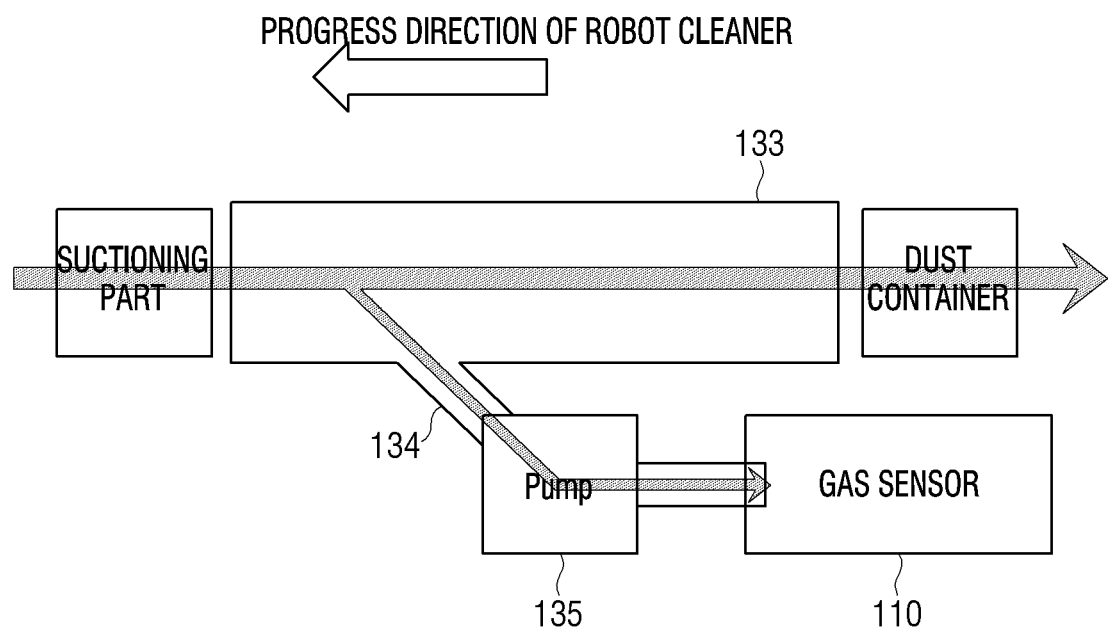

Meanwhile, if necessary, the robot cleaner 100 may further include a pump 135 arranged on the sub flow path 134 as illustrated in FIG. 8. Here, the pump 135 may, based on sensing being difficult because the flow amount and the flow rate of air which flows through the sub flow path 134 is too low, be a configuration for further introducing air to the gas sensor 110. The pump 135 may further suction air from the main flow path 133 and provide air which is improved in flow amount and flow rate to the gas sensor 110.

Meanwhile, in the above, the gas sensor has been described as being arranged outside or inside of the robot cleaner, but at actual implementation, it may be arranged at both the outside and the inside.

Figure 9:
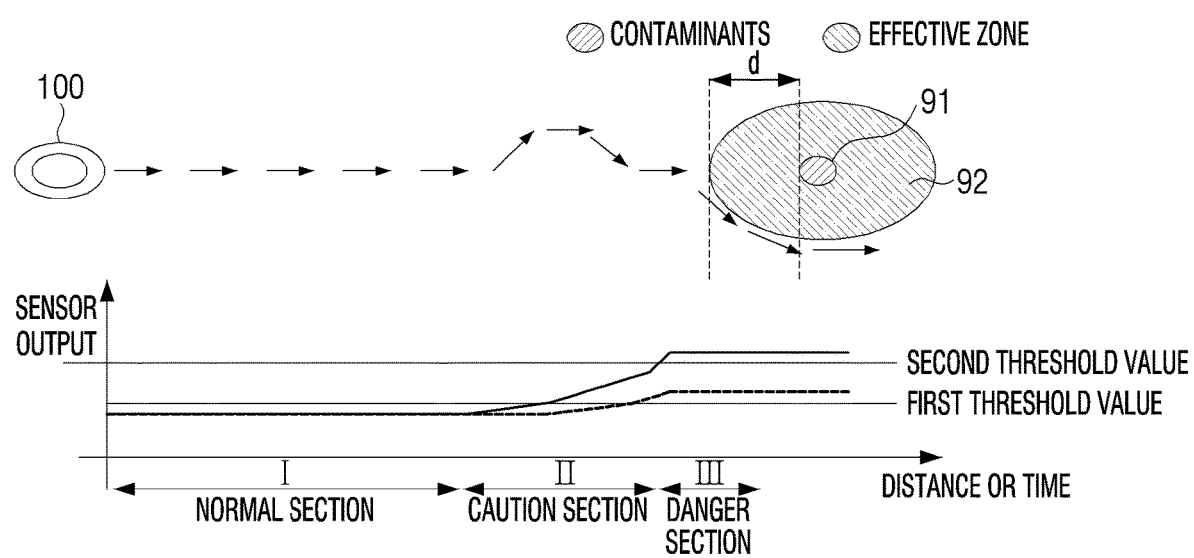
FIG. 9 is a diagram illustrating an operation of a robot cleaner according to a sensing value of a gas sensor.

FIG. 9 is a diagram illustrating an operation of a robot cleaner according to a sensing value of a gas sensor. Specifically, in FIG. 9, an embodiment of a sensor output value being sensed as the robot cleaner 100 approaches the contaminants 91 may be verified. Here, the solid line represents an output value of the sensor arranged at the left side of the front surface of the robot cleaner 100, and the dotted line represents the output value of the sensor arranged at the right side of the front surface of the robot cleaner 100.

Referring to FIG. 9, based on the output values of both sensors being both less than a first threshold value, the robot cleaner 100 may identify as a normal section I. The normal section may refer to the robot cleaner 100 being a cleaning mode, and may be a section in which the direction and the speed are maintained.

Meanwhile, based on the output value of at least one sensor from among both sensors exceeding the first threshold value and the output values of both sensors being both less than a second threshold value, the robot cleaner may identify as a caution section II. The caution section may refer to a section in which the driving speed of the robot cleaner 100 is reduced. Based on reducing the speed of the robot cleaner 100, the time for sensing the gas may be secured.

Meanwhile, based on the output value of at least one sensor from among both sensors exceeding the second threshold value, the robot cleaner 100 may identify as a danger section III. Here, the danger section may refer to identifying the effective zone 92 based on prediction of the zone of contaminants 91 and the sensor output value.

Specifically, the robot cleaner 100 may change, based on the output value of at least one sensor from among both sensors exceeding the second threshold value, the driving direction. For example, the driving direction may be changed to a direction with a low sensing value from among both sensors. At this time, the driving speed may be lower than the speed in the caution section.

Further, the degree of change of the driving direction may be determined based on the sensing values of both sensors. This is for the tracking of the effective zone 92, and the driving direction may be changed so that the output values of both sensors maintain a value of a certain degree by changing the driving direction to a direction with a low sensing value from among both sensors, but not fully exceeding the effective zone 92.

For example, referring to FIG. 9, the robot cleaner 100 may, in order to maintain the sensing value of the left side sensor near the second threshold value, perform tracking of the effective zone 92 by changing the driving direction so that the sensing value of the right side sensor is maintained at a value lower than the second threshold value.

Meanwhile, a distance d from a boundary of the effective zone 92 to the contaminants 91 may be represented by a multiplication of the driving speed of the robot cleaner 100 and a difference in response time $\Delta t$ of both sensors. For example, the difference in response time $\Delta t$ of both sensors may refer to the difference in time spent in sensing a specific sensing value.

Then, the robot cleaner 100 may predict, based on the tracking of the effective zone 92 being complete, the position at which the contaminants 92 are present based on the tracked effective zone 92. This will be described below with reference to FIG. 10. Here, the tracking of the effective zone 92 being complete may refer to the robot cleaner 100 performing the tracking of the effective zone 92 and returning back to an initial position in which the driving direction is changed based on the gas sensing value. Meanwhile, based on the tracking of the effective zone 92 being complete, the robot cleaner 100 may drive to an area other than the effective zone 92 and resume the cleaning mode.

Figure 10:
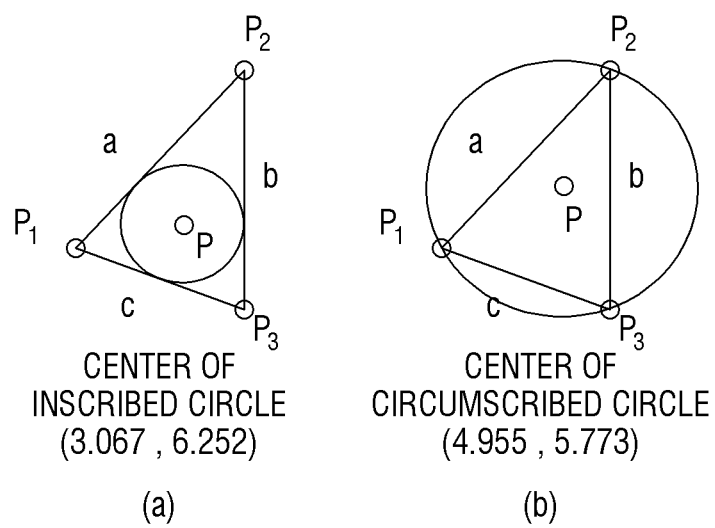
FIG. 10 is a diagram illustrating an embodiment calculating a position of contaminants.

FIG. 10 is a diagram illustrating an embodiment calculating a position of contaminants.

Referring to FIG. 10, the robot cleaner may obtain three or more points $P_1$, $P_2$ and $P_3$ based on the sensing value while tracking the effective zone. At this time, the point to be obtained may be a point in which the sensing value is greater than or equal to a pre-set value. Further, the position information of each point may be obtained through GPS.

The robot cleaner may obtain straight line distances a, b and c between each of the points. Then, the robot cleaner may calculate an arbitrary concentration gradient area which uses the output characteristics of a sensor. Specifically, the robot cleaner may calculate a center coordinate of an inscribed circle of an area which connects each of the points as illustrated in FIG. 10(a) as the position P of the contaminants, or as illustrated in FIG. 10(b), calculate a center coordinate of a circumscribed circle of an area which connects each of the points as the position P of the contaminants. Meanwhile, predicting the position P of the above-described contaminants is merely one embodiment, and is not limited thereto.

Meanwhile, although not illustrated, the robot cleaner may display the position and size of the contaminants based on a calculated result value to the stored indoor structure image and transmit to the user terminal device or the external server. At this time, not only the information on the position and size of the contaminants, but also the type of the contaminants may be transmitted.

FIG. 11 is a flowchart illustrating a control method of a robot cleaner according to an embodiment of the disclosure.

Referring to FIG. 11, the robot cleaner may first sense the gas of the air suctioned inside the robot cleaner (S1110). At this time, the robot cleaner may use the gas sensor arranged inside the robot cleaner to sense the gas of the drawn-in air. Meanwhile, the gas sensor may be arranged on the main flow path through which the drawn-in air flows. In another embodiment, the gas sensor may be branched from the main flow path and arranged at the end of the sub flow path through which a portion of the drawn-in air flows.

The, the robot cleaner may identify the contaminants based on the sensing value of the air (S1120). Specifically, the robot cleaner may identify whether contaminants are present and the type of the contaminants based on the sensing value obtained by the gas sensor. For example, the robot cleaner may detect the presence of contaminants in its surroundings, particularly at the front. Then, based on the result of analyzing the sensing value, if the concentration of ammonia is greater than or equal to a pre-set value, the robot cleaner may identify the contaminants as urine, and if the concentration of sulfur compounds is greater than or equal to a pre-set value, the robot cleaner may identify the contaminants as excrement.

Then, the robot cleaner may drive avoiding the identified contaminants (S1130). Specifically, the robot cleaner may, based on the sensing value being greater than or equal to a pre-set value based on the gas sensing value of air, reduce the driving speed and secure time for detecting the gas discharged from the contaminants.

Then, the robot cleaner may rotate, based on the sensing value being greater than or equal to a pre-set value, the robot cleaner left and right by a pre-set angle and change the driving direction to a direction with a low sensing value. In case a plurality of gas sensors is arranged at both sides of the front surface of the robot cleaner, the driving direction may be changed to a direction the sensor with the low sensing value is arranged from among both sensors. Accordingly, driving by avoiding the contaminants may be possible Meanwhile, the robot cleaner may perform tracking of the position of the contaminants and the size of the area while changing driving direction. Then, the robot cleaner may transmit the information on the position of the contaminants and the size of the area to the external device. At this time, the robot cleaner may also transmit information on the type of the contaminants therewith.

According to the various embodiments described above, the robot cleaner may drive avoiding the contaminants, and may transmit the type, position and size information of the contaminants to the user so that the user is able to remove the contaminants.

The various embodiments described above may be implemented in a recordable medium which is readable by a computer or a device similar to the computer using software, hardware, or the combination of software and hardware. By hardware implementation, the embodiments of the disclosure may be implemented using at least one from among application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, or electric units for performing other functions. In some cases, embodiments described herein may be implemented by the processor itself. According to a software implementation, embodiments such as the procedures and functions described herein may be implemented with separate software modules. Each of the above-described software modules may perform one or more of the functions and operations described herein.

Meanwhile, a method according to one or more embodiments disclosed in the disclosure may be stored in a non-transitory readable medium. The non-transitory readable medium as described above may be mounted to various devices and used.

The non-transitory readable medium may refer to a medium that stores data semi-permanently rather than storing data for a very short time, such as a register, a cache, a memory, or the like, and is readable by a device. Specifically, the programs for performing the above-described various methods may be stored and provided in the non-transitory readable medium such as, for example, and without limitation, a compact disc (CD), a digital versatile disc (DVD), a hard disc, a Blu-ray disc, a USB, a memory card, a ROM, and the like.

According to an embodiment, a method according to one or more embodiments disclosed in the disclosure may be provided included a computer program product. The computer program product may be exchanged between a seller and a purchaser as a commodity. The computer program product may be distributed in the form of a machine-readable storage medium (e.g., a compact disc read only memory (CD-ROM)), or distributed online through an application store (e.g., PLAYSTORE™). In the case of online distribution, at least a portion of the computer program product may be at least stored temporarily in a storage medium such as a server of a manufacturer, a server of an application store, or a memory of a relay server, or temporarily generated.

Further, while the disclosure has been shown and described with reference to the exemplary embodiments thereof, the disclosure is not limited to the embodiments specifically described above and various modifications may be made therein by those skilled in the art to which this disclosure pertains without departing from the spirit and scope of the disclosure, and such modifications shall not be understood as separate from the technical concept or outlook of the present disclosure.

What is claimed is:

1. A robot cleaner, comprising:
   a driving part configured to drive and steer the robot cleaner in a progress direction;
   a suctioning part;
   a gas sensor disposed inside of the robot cleaner and configured to sense drawn-in air, wherein the gas sensor is disposed ahead of the suctioning part along the progress direction when the robot cleaner is moving in the progress direction and sensing the drawn-in air; and
   a processor configured to identify contaminants based on a sensing value of the gas sensor, and control the driving part to change the progress direction to a second progress direction leading away from the identified contaminants.

2. The robot cleaner of claim 1, wherein
   the robot cleaner provides:
   a main flow path through which air from outside the robot cleaner flows into the robot cleaner; and
   a sub flow path which is branched from the main flow path, and through which a portion of the air in the main flow path flows through, and
   wherein the gas sensor is arranged at an end of the sub flow path, and configured to sense the air flowing through the sub flow path.

3. The robot cleaner of claim 2, further comprising:
   a pump arranged in the sub flow path.

4. The robot cleaner of claim 1, wherein the processor is configured to reduce, based on a sensing value of the gas sensor being greater than or equal to a pre-set value, a driving speed of the robot cleaner.

5. The robot cleaner of claim 4, wherein the processor is configured to control, based on a sensing value of the gas sensor being greater than or equal to a pre-set value, the robot cleaner to rotate left and right by a pre-set angle to obtain a sensing value from the gas sensor, and drive in a direction in which the obtained sensing value is less than the pre-set value.

6. The robot cleaner of claim 5, wherein the processor is configured to identify, based on a sensing value of the gas sensor being greater than or equal to a pre-set value, a position of the contaminants and a size of an area based on a driving route.

7. The robot cleaner of claim 6, further comprising:
a communicator configured to communicate with an external device,
wherein the processor is configured to transmit information on the identified position of the contaminants and the size of the area to the external device.

8. The robot cleaner of claim 1, further comprising:
a second gas sensor arranged at an outer front surface of the robot cleaner based on a driving direction of the robot cleaner.

9. The robot cleaner of claim 8, wherein the second gas sensor is arranged at a left side and a right side of the front surface of the robot cleaner, and
wherein the processor is configured to control, based on a sensing value of the second gas sensor of at least one of the left side or the right side being greater than or equal to a pre-set value, the robot cleaner to drive in a direction in which the sensing value is less than the pre-set value.

10. The robot cleaner of claim 1, wherein the processor is configured to analyze a type of gas based on a value sensed by the gas sensor, and identify a type of contaminants based on the type of gas.

11. A method for controlling a robot cleaner, the method comprising:
at the robot cleaner, wherein the robot cleaner comprising a driving part configured to drive and steer the robot cleaner in a progress direction, a suctioning part, and a gas sensor disposed inside the robot cleaner ahead of the suctioning part along the progress direction when the robot cleaner is moving in the progress direction and sensing drawn-in air, sensing gas in air drawn-in inside of the robot cleaner by using the gas sensor;
identifying contaminants based on a sensing value of the air; and
controlling the driving part to change the progress direction to a second progress direction leading away from the identified contaminants.

12. The method of claim 11,
wherein the robot cleaner provides:
a main flow path through which air from outside the robot cleaner flows into the robot cleaner, and
a sub flow path which is branched from a main flow path through which a portion of the air in the main flow path flows,
wherein the gas sensor is arranged at an end of the sub flow path and configured to sense the air flowing in the sub flow path.

13. The method of claim 12, wherein the sensing further comprises:
introducing air flowing in the sub flow path to the gas sensor by using a pump arranged at the sub flow path.

14. The method of claim 11, wherein the driving comprises reducing, based on a sensing value of the gas sensor being greater than or equal to a pre-set value, a driving speed of the robot cleaner.

15. The method of claim 14, wherein the driving comprises rotating, based on a sensing value of the gas sensor being greater than or equal to a pre-set value, left and right by a pre-set angle to obtain a sensing value from the gas sensor, and driving in a direction in which the obtained sensing value is less than the pre-set value.

* * * * *